United States Patent
Klootz

(10) Patent No.: US 7,041,054 B2
(45) Date of Patent: May 9, 2006

(54) LED ILLUMINATION FOR SURGICAL ENDOSCOPES AND INDUSTRIAL RIGID BOROSCOPES

(76) Inventor: Jack Klootz, 6005 Pinnacle La., #402, Naples, FL (US) 34110

(*) Notice: Subject to any disclaimer, the term of this patent is extended or adjusted under 35 U.S.C. 154(b) by 0 days.

(21) Appl. No.: 10/711,005

(22) Filed: Aug. 17, 2004

(65) Prior Publication Data

US 2006/0041192 A1   Feb. 23, 2006

(51) Int. Cl.
*A61B 1/07* (2006.01)
*G02B 6/25* (2006.01)

(52) U.S. Cl. ............... 600/178; 600/132; 600/182; 362/555; 362/574; 385/117

(58) Field of Classification Search ........ 600/178, 600/179, 182, 132; 362/555, 574, 572; 385/88, 385/117, 902
See application file for complete search history.

(56) References Cited

U.S. PATENT DOCUMENTS

| 3,261,349 | A | * | 7/1966 | Wallace | 600/135 |
| 4,019,805 | A | * | 4/1977 | Marcatili et al. | 385/89 |
| 4,241,382 | A | * | 12/1980 | Daniel | 362/581 |
| 4,823,244 | A | * | 4/1989 | Alaybayoglu et al. | 362/194 |
| 5,647,840 | A | * | 7/1997 | D'Amelio et al. | 600/169 |
| 5,791,965 | A | * | 8/1998 | Kim | 446/219 |
| 6,007,485 | A | * | 12/1999 | Koeda et al. | 600/178 |
| 6,277,064 | B1 | | 8/2001 | Yoon | |
| 6,692,432 | B1 | * | 2/2004 | Yarush et al. | 600/179 |
| 2002/0028986 | A1 | * | 3/2002 | Thompson | 600/178 |
| 2002/0089586 | A1 | * | 7/2002 | Suzuki et al. | 348/68 |
| 2002/0120181 | A1 | * | 8/2002 | Irion | 600/178 |
| 2004/0186352 | A1 | * | 9/2004 | Roberts et al. | 600/200 |

* cited by examiner

Primary Examiner—John P. Leubecker
(74) Attorney, Agent, or Firm—Malin, Haley & DiMaggio, P.A.

(57) ABSTRACT

An endoscope and stroboscope comprising an elongated rigid tube that includes an inner tube providing an optical path for viewing through said tube by a human being, an LED light source connected to said tube and a fiber optic bundle providing light transmission from said LED through and within said endoscopic and stroboscopic tube providing optical illumination from the distal end of said tube without interfering with the optical view for the user. The LED light source can be varied in intensity. A first end of the fiber optic bundle is a hemispherical concave shape abuts the LED light source.

2 Claims, 4 Drawing Sheets

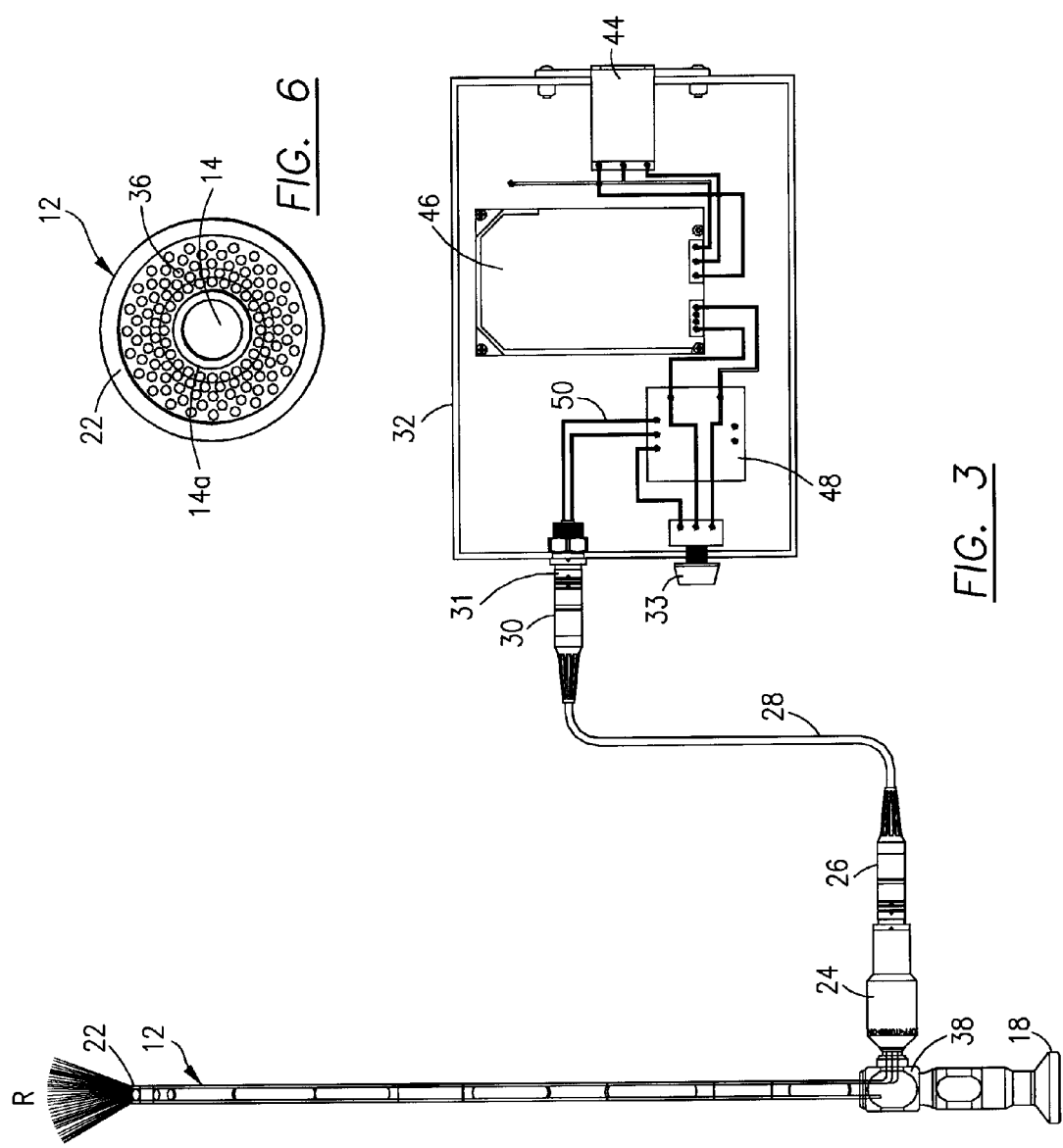

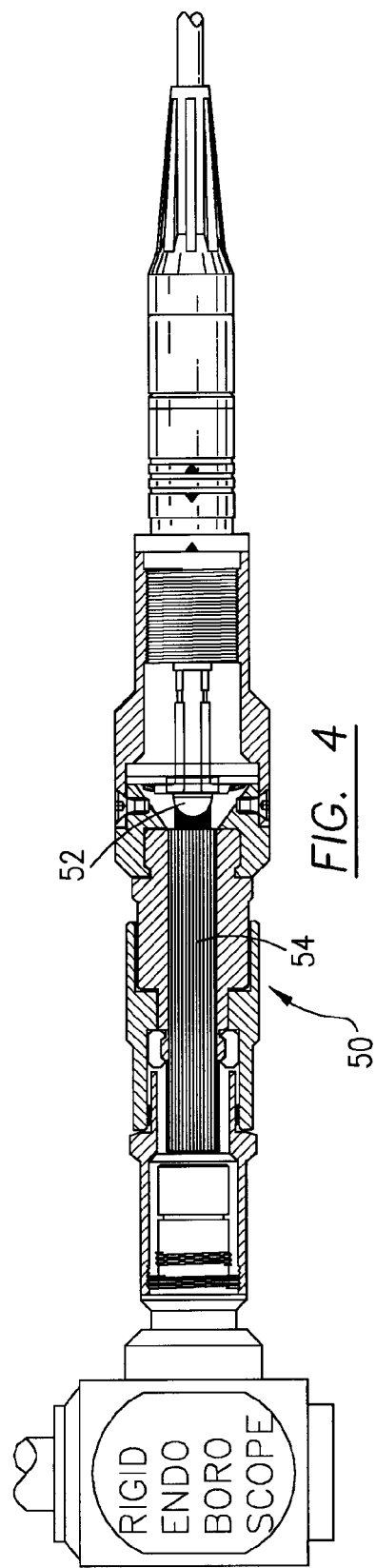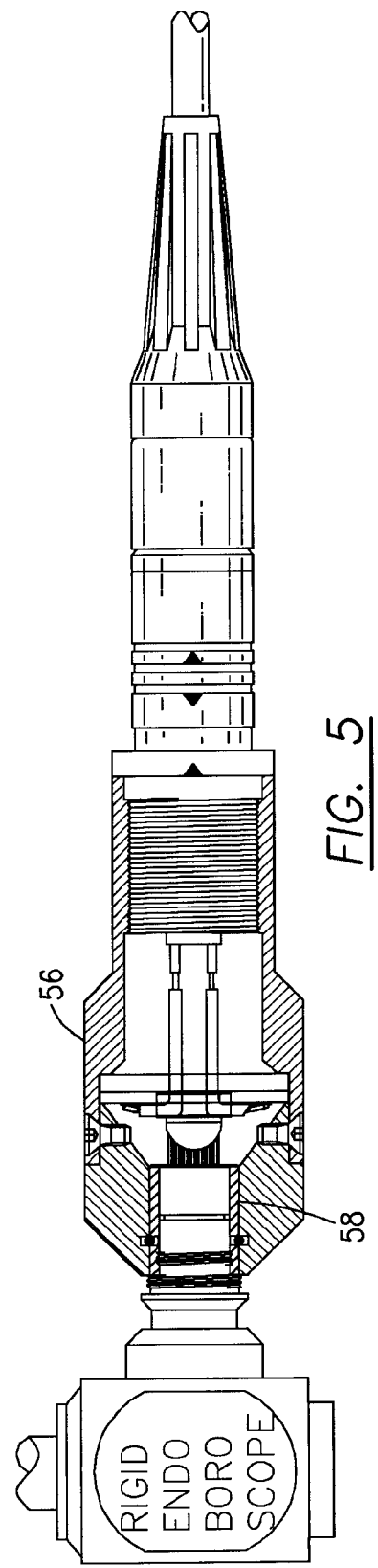

LED ILLUMINATION FOR SURGICAL ENDOSCOPES AND INDUSTRIAL RIGID BOROSCOPES

BACKGROUND OF INVENTION

Field of the Invention

This invention relates to surgical endoscopes and industrial boroscopes and an illumination device used therein and, specifically, to an improved surgical endoscope and industrial boroscope that utilizes an LED light in combination with fiber optic bundles for illumination.

Description of Related Art

Surgical endoscopes have long been known for probing hollow organs. Likewise, industrial boroscopes have been used for investigating hard to reach places for industrial purposes. One of the important aspects of a surgical endoscope or an industrial boroscope is that it provides an optically clear view of the organ or area under investigation to someone that is looking through the endoscope or the boroscope in real time. Various types of illumination have been used with endoscopes and boroscopes in the prior art. One of the problems experienced with an endoscope or a boroscope is that the optical path from the eye of the user to the object or organ being investigated also needs to provide for illumination without interrupting the visual observation path. Thus, the end point of the endoscope or boroscope needs some form of illumination that does not interfere with the clear visual and optical path from the eye of the user to the object under investigation. U.S. Pat. No. 6,277,064 issued to Yoon on Aug. 21, 2001 shows a surgical endoscope that has a rotatably mounted offset shaft. This is to accommodate the illumination of the organ while, at the same time, not disturbing the optical view through the endoscope. By placing the illumination source, such as an LED, at the very end of the device on a separate shaft, the light source may not provide proper illumination distribution on the particular hollow organ or object being viewed. The present invention overcomes the problems shown in the prior art by providing a light illumination pattern that emanates around the optical path at the end of the endoscope or boroscope through the use of an LED light source mounted well up-stream and fiber optic strands that surround the optical, visual path terminating at a distal end and providing for a uniformly distributed light pattern.

SUMMARY OF INVENTION

An endoscope or boroscope comprising an elongated, cylindrical, hollow tube having a proximal end and a distal end. An eyepiece for viewing through the tube by the user is attached coaxially to the distal end of the hollow tube through a mounting block that is also attached to an illumination housing which is also a handle. The rigid hollow tube includes a plurality of optical lenses disposed internally along its length and is aligned coaxially with the eyepiece attached to the distal end. The eyepiece includes an eyepiece housing and may include a shield.

A plurality of fiber optic strands forming a bundle are disposed on the inside periphery of the elongated hollow rigid tube surrounding the optical lens devices that are mounted within the tube.

An illumination housing is detachably connected to the mounting block at approximately a 90 degree angle. Inside the illumination housing is an LED light source (light emitting diode) and the distal end of the fiber optic bundle distributed throughout the elongated tube which is disposed directly against the LED illumination surface for direct light transmission from the LED into each end of each fiber optic strand. The fiber optic strands are mounted in a rigid cylindrical housing which can be detachably connected to the elongated tube through the mounting block. The LED light illumination housing also includes a connection to an electrical power cable comprising a pair of electrical conductors that are connected to an electrical power source that provides DC voltage and current to the LED through the pair of conductors. The LED electrodes are connected to the electrical conductors' power source within the LED light illumination housing. The power cable that is connected to the power source can be detached from the LED light illumination housing.

The invention includes a direct current (DC) power source and power panel that is a rigid box that houses a transformer that changes 90–264 volts AC at 47–63 Hz frequency into a 12 volt DC power supply to the LED of 500 milliamps. The power panel also includes a rheostat for controlling the amount of current to the LED through the cable and an on/off switch.

In operation, the power panel is connected to a conventional 90–264 volt AC at 47–63 Hz frequency outlet. In order to use the endoscope, the power switch is turned on and the amount of light intensity is adjusted for the specific job to be performed with the endoscope or the boroscope. The operator, such as a doctor or surgeon, will look through the eyepiece and while inserting the probe into a person to investigate an organ. The light source from the LED transmits illumination and light through the fiber optic bundles so that the light radiates from the end of the endoscope onto the organ being investigated. At the proximal end of the elongated tube, the proximal ends of the fiber optic bundle are disposed around the inside periphery of the tube and the internal lenses. Each fiber optic strand emanates light out of the proximal end of the tube. The light source is the LED. A spherical pattern of light is emitted from the tube and illuminating the portion of the body or object near the proximal end.

It is an object of this invention to provide an improved endoscope and boroscope that utilizes an LED light source and fiber optic bundle for improved illumination.

It is another object of this invention to provide an improved endoscope and boroscope that includes a detachable housing that contains an LED light source and coaxial bundle that is transmitted down the endoscopic and boroscopic tube for emanation at the distal end of the tube, thereby illuminating the object of interest for the user.

In accordance with these and other objects which will become apparent hereinafter, the instant invention will now be described with particular reference to the accompanying drawings.

BRIEF DESCRIPTION OF DRAWINGS

FIG. 3 shows a schematic diagram of the present invention including the power supply.

FIG. 4 shows a side elevational view of an alternate embodiment of the light housing.

FIG. 5 shows yet another alternate embodiment of the present invention in a side elevational cross section view of the light housing.

FIG. 6 shows an end elevational view of the proximal end of the endoscope.

DETAILED DESCRIPTION

Figure 1:
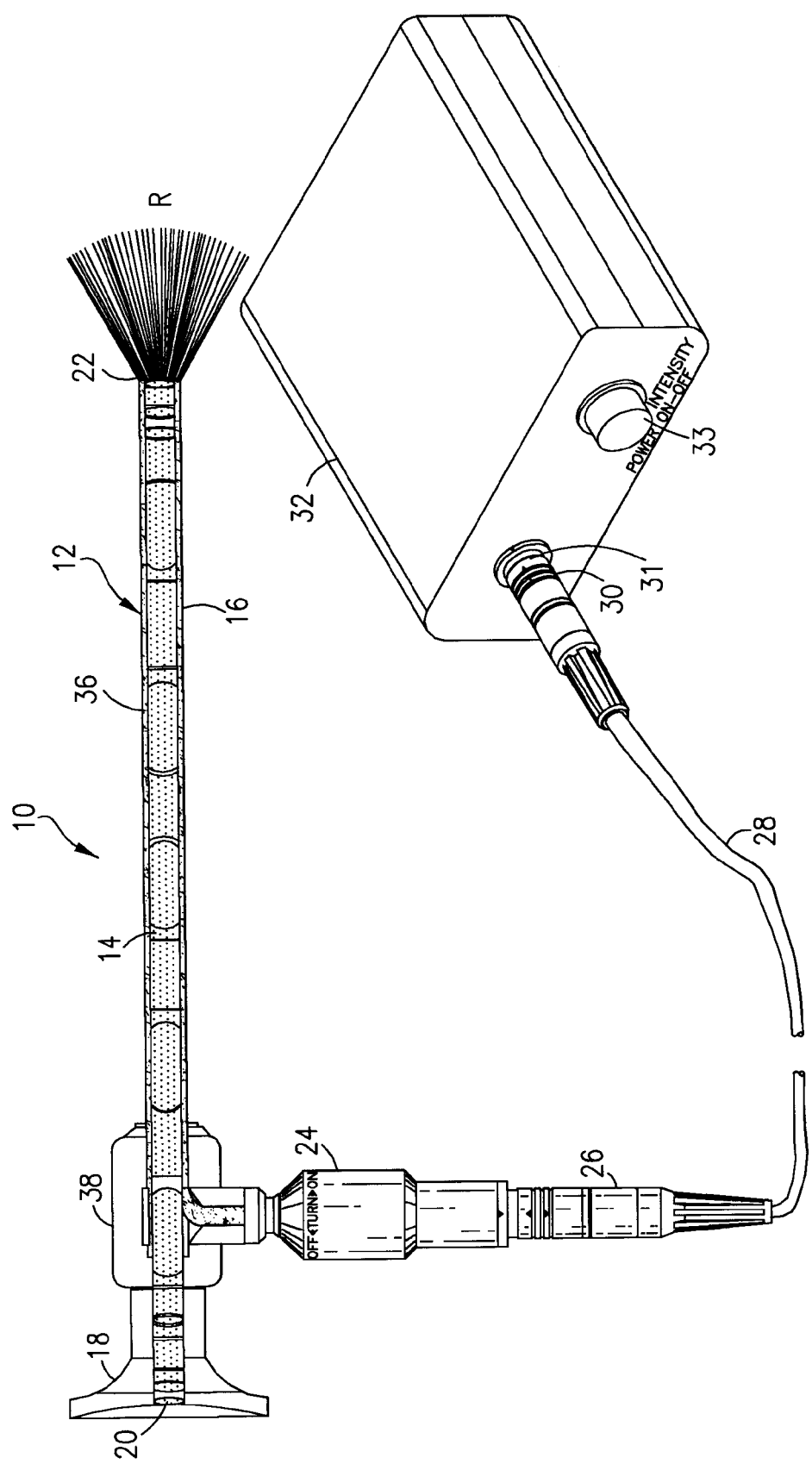
FIG. 1 shows a side elevational view partly in cross section and partially in perspective of the present invention.

Referring now to the drawings, the present invention is shown generally at 10 that includes an endoscopic tube 12 that includes optical lenses 14 disposed along its internal length. The endoscopic tube 12 is a hollow straight, rigid tube preferably made out of metal that permits an optical path through its center from the distal end 22 to the eyepiece 18 which is at the proximal end 20. Rays of light "R" are shown emanating from the distal end 22. As shown in the central portion of the tube, there are lenses 14 disposed in an inner tube 14a (FIG. 6) so that a person could look through the eyepiece 18 and observe a hollow organ or machine part through the distal end 22.

An LED housing 24 is preferably attached perpendicularly to the endoscopic tube 12 through a mounting block 38. The LED housing 24 is detachably connected to a long power cable 28 through a push/pull detachable coupler 26 and the push/pull detachable coupler 30 that plugs into power supply plug 31 in power supply box 32. The endoscope LED DC power source has an on/off switch 33 that also can be rotated to vary the current and, therefore, the light intensity emanating from the LED that is mounted inside of housing 24. A fiber optic illumination bundle 36 is mounted around the inside periphery of the endoscopic tube 12 and is explained in greater detail below.

Figure 2:
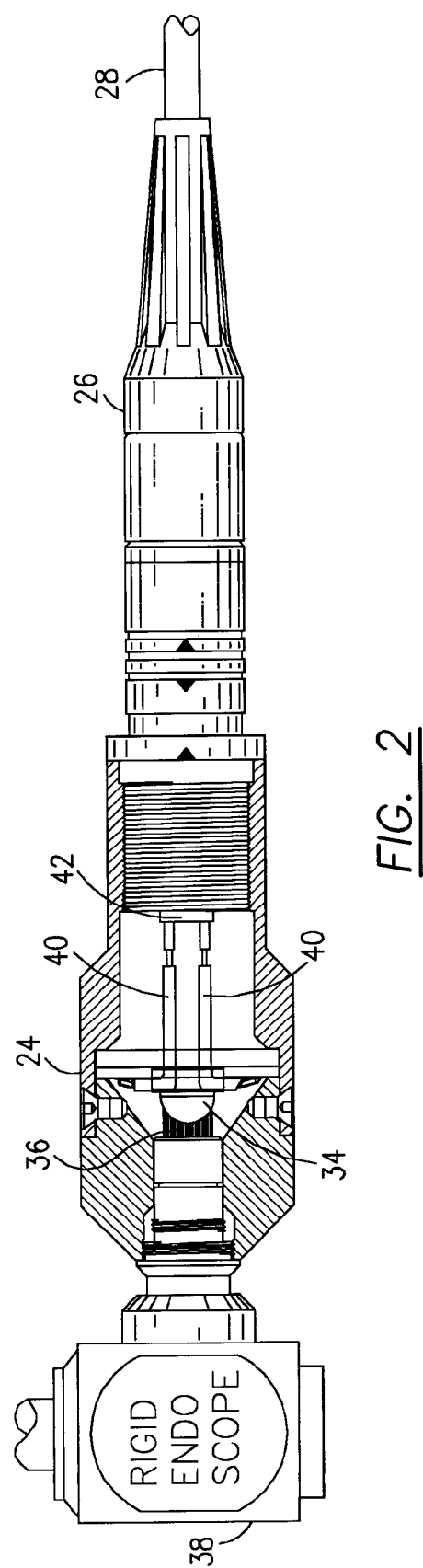
FIG. 2 shows a side elevational view partly in cross section of the LED light housing used in the present invention.

Referring now to FIG. 2, a light emitting diode (LED) 34 is shown having a pair of electrodes 40 that connect to the power source through electrodes 42 from cable 28. Abutting the surface of LED 34 is a fiber optic bundle 36 that continues through tube 12 to the distal end 22. The hemispherical concave shape of the portion of the fiber optic bundles that cover the surface of LED at 36 is preferred so that each fiber optic strand can transmit the maximum light from LED 34 to the distal end 22 of the endoscopic tube 12. The detachable coupler 26 is used to connect the power source to the LED 34.

Referring now to FIG. 3, the overall system is shown including the endoscopic tube 12 connected to the LED housing 24 through a mounting block 38 which is connected directly to the endoscopic tube 12 and secures the light housing 24 in a generally perpendicular direction to the endoscopic tube 12. Also schematically shown in FIG. 3 is the DC power source box 32 which has housed therein a transformer 46 connected to a 90–264 Vac/47–63 Hz input receptacle 44 that can be plugged into a conventional AC power supply. The transformer 46 creates 12 volt DC voltage and a 500 milliamp current which is supplied to the rheostat current intensity control 48 and the rotatable switch 33 which is also preferably the on/off switch. Twelve volt DC is provided through electrical connectors 50 to the power plug 31, detachable coupler 30.

In order to operate the invention, the user would turn switch 33 on and adjust the light intensity to suit a particular situation. The endoscopic tube 12 can also be a stroboscope for industrial purposes. Once the light intensity is chosen, which can be varied during the operation, a surgeon would look through eyepiece 18 after the probe or strobe tube 12 has been inserted in the patient. Light from LED 34 would be transmitted through the fiber optic bundle and radiate out the distal end 22 of the endoscope or stroboscope illuminating the subject matter with rays "R" surrounding the distal end 22 of the probe at 12. The light intensity can be varied by rotating switch 33. Note that the location of the illumination source at the distal end 22 which surrounds the endoscopic tube optical path does not interfere with the optical path but provides direct illumination from the end of the tube.

FIG. 4 shows an alternate embodiment of the invention that has a different LED housing for LED 52 with the fiber optic bundles 54 being mounted within a housing 50 which itself is then connected to the endoscopic tube 12 as described above. The operation is the same as described above with respect to the illumination provided by LED 52 at the distal end of the endoscopic tube 12.

FIG. 5 shows yet another embodiment of the invention. In FIG. 5, the housing 56 is connection to the endoscopic tube through a universal connector 58. Thus, housing 56 may be exchanged in accordance with particular situations, such as a situation where a different colored light is required. Also, the housing 56 may be replaced in case of a failure.

FIG. 6 shows the light emitting distal end 22 of the endoscope tube 12 that includes the distal ends of each of the fiber optic strands 36 that emit light transmitted from the LED. The optic lenses 14 are mounted in a small inner tube 14a. The fiber optic bundle 36 is mounted around the outside of tube 14a and inside tube 12.

The benefits of using an LED and the fact that the LED can be mounted in such a way and provided in conjunction with the fiber optic bundles as described in the present invention greatly improve the illumination of the subject matter while not interfering with the surgeon or user's direct optical path view of the object in question. The unit is safe and the illumination pattern is controllable.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A viewing tube for use as an endoscope or stroboscope that includes an LED illumination source comprising:
    a straight, elongated, rigid hollow outer tube;
    a coaxial smaller inner tube;
    one or more optical lenses disposed within said inner tube forming an optical path allowing human observation from a proximal end of said tube to a distal end of said tube;
    an eyepiece for human observation mounted at the proximal end of said tube;
    an LED light housing including an LED light source mounted within said LED light housing;
    a mounting block for mounting said LED light housing substantially perpendicular to said elongated rigid tube;
    a fiber optic bundle having a first end abutting said LED light source to receive light for transmission there through, said fiber optic bundle having a portion connected and surrounding said inner tube and said lens optical path within said inner tube, said fiber optic bundle having a second light emanating end mounted at the distal end of said tube for an illumination pattern emanating from the distal end of said tube;
        wherein a portion of the first end of the fiber optic bundle that covers a surface of the LED light source and has a hemispherical concave shape; and
    a power source connected to said LED light source for providing electrical power for illuminating said LED light source.

2. The invention of claim 1, wherein the hemispherical concave shape of the portion of the fiber optic bundle that covers the surface of the LED light source allows each fiber optic strand of the fiber optic bundle to transmit the maximum light from said LED light source to the distal end of the endoscopic inner tube.

* * * * *